US012446941B2

(12) United States Patent
Spreiter et al.

(10) Patent No.: US 12,446,941 B2
(45) Date of Patent: Oct. 21, 2025

(54) SELF-RETAINING SCREWDRIVER WITH SLOTTED TIP

(71) Applicant: DEPUY SYNTHES PRODUCTS, INC., Raynham, MA (US)

(72) Inventors: Gregor Spreiter, Zuchwil (CH); Henri Défossez, Neuchatel (CH); André Weber, Olten (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 1107 days.

(21) Appl. No.: 16/851,083

(22) Filed: Apr. 16, 2020

(65) Prior Publication Data

US 2021/0322076 A1 Oct. 21, 2021

(51) Int. Cl.
*A61B 17/88* (2006.01)
*A61B 17/16* (2006.01)
*A61B 17/00* (2006.01)

(52) U.S. Cl.
CPC ........ *A61B 17/888* (2013.01); *A61B 17/1633* (2013.01); *A61B 17/164* (2013.01); *A61B 2017/00473* (2013.01)

(58) Field of Classification Search
CPC .... A61B 17/888; A61B 17/133; A61B 17/164
See application file for complete search history.

(56) References Cited

U.S. PATENT DOCUMENTS 4,140,161 A 2/1979 Russo et al.
5,423,819 A 6/1995 Small et al.
5,605,080 A 2/1997 Pfefferle et al.
5,649,931 A 7/1997 Bryant et al.
6,626,907 B2 9/2003 Campbell et al.
7,174,615 B2 2/2007 Mark et al.
8,763,499 B2 7/2014 Dahners
8,777,960 B2 * 7/2014 Murray .............. A61B 17/8888 606/104
8,808,307 B2 8/2014 Robinson
8,906,077 B2 12/2014 Bush, Jr. et al.
9,078,717 B2 7/2015 Griffiths et al.
9,113,970 B2 8/2015 Lewis et al.
2003/0187447 A1 10/2003 Ferrante et al.
2005/0033307 A1 2/2005 Cook et al.
2007/0010821 A1 1/2007 Wilkinson et al.

(Continued)

FOREIGN PATENT DOCUMENTS

DE 3804749 3/1989
DE 3816718 11/1989

(Continued)

*Primary Examiner* — Sameh R Boles

(74) *Attorney, Agent, or Firm* — Fay Kaplun & Marcin, LLP

(57) ABSTRACT

A screwdriver includes a body extending longitudinally from a proximal end to a distal end. The distal end includes a distal screw engaging tip. The screwdriver also includes a slot extending through a width of the screw engaging tip and extending proximally a distance into the body. The slot permits opposed portions of the screw engaging tip to spread apart from one another into a locking configuration in which the opposed portions apply a radially outward force against an interior surface of a recess in a head of a screw into which the screw engaging tip has been inserted to releasably lock the screw engaging tip within the recess.

5 Claims, 3 Drawing Sheets

(56) References Cited

U.S. PATENT DOCUMENTS

| | | | |
|---|---|---|---|
| 2008/0041196 | A1 | 2/2008 | Companioni et al. |
| 2008/0269768 | A1 | 10/2008 | Schwager et al. |
| 2009/0275992 | A1 | 11/2009 | Phan et al. |
| 2009/0326545 | A1 | 12/2009 | Schaffhausen |
| 2010/0312279 | A1* | 12/2010 | Gephart ........... A61B 17/00234 606/279 |
| 2011/0098715 | A1 | 4/2011 | Laubert et al. |
| 2013/0129447 | A1 | 5/2013 | Canizares, Jr. et al. |
| 2013/0150864 | A1 | 6/2013 | Marik et al. |
| 2013/0184749 | A1 | 7/2013 | Lore et al. |
| 2013/0226191 | A1 | 8/2013 | Thoren et al. |
| 2013/0226239 | A1 | 8/2013 | Altarac et al. |
| 2014/0194936 | A1 | 7/2014 | Hawkes et al. |
| 2015/0142066 | A1 | 5/2015 | Shemwell et al. |
| 2015/0150605 | A1 | 6/2015 | Saidha et al. |
| 2015/0238236 | A1 | 8/2015 | Sasing |
| 2015/0250506 | A1 | 9/2015 | Philippon |
| 2015/0250520 | A1 | 9/2015 | Rezach et al. |
| 2016/0135852 | A1 | 5/2016 | Altarac et al. |
| 2016/0235457 | A1 | 8/2016 | Santangelo et al. |
| 2016/0249965 | A1 | 9/2016 | Jerke |
| 2016/0262819 | A1 | 9/2016 | May et al. |
| 2016/0270831 | A1 | 9/2016 | Perrow et al. |

FOREIGN PATENT DOCUMENTS

| | | |
|---|---|---|
| DE | 19851370 | 5/2000 |
| EP | 0222971 | 5/1987 |
| EP | 1192912 | 4/2002 |
| EP | 1938766 | 7/2008 |
| EP | 2131770 | 12/2009 |
| EP | 2460485 | 6/2012 |
| EP | 2626019 | 8/2013 |
| EP | 2724682 | 4/2014 |
| EP | 2799023 | 11/2014 |
| EP | 2898853 | 7/2015 |
| EP | 2918238 | 9/2015 |
| EP | 3020348 | 5/2016 |
| EP | 3069672 | 9/2016 |
| GB | 2513436 | 10/2014 |
| WO | 2007/003113 | 1/2007 |
| WO | 2008/122446 | 12/2008 |
| WO | 2012/134437 | 10/2012 |
| WO | 2012/134628 | 10/2012 |
| WO | 2014/204076 | 12/2014 |

* cited by examiner

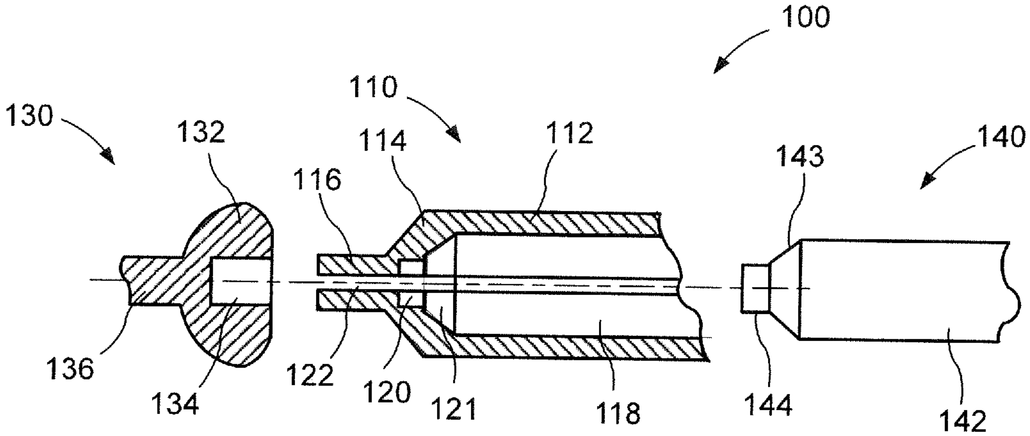
F I G. 1
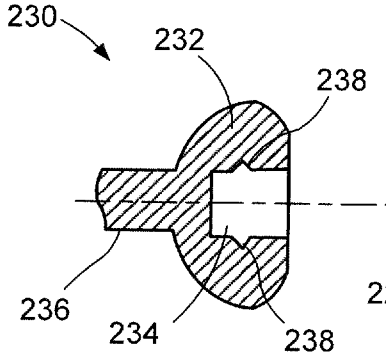
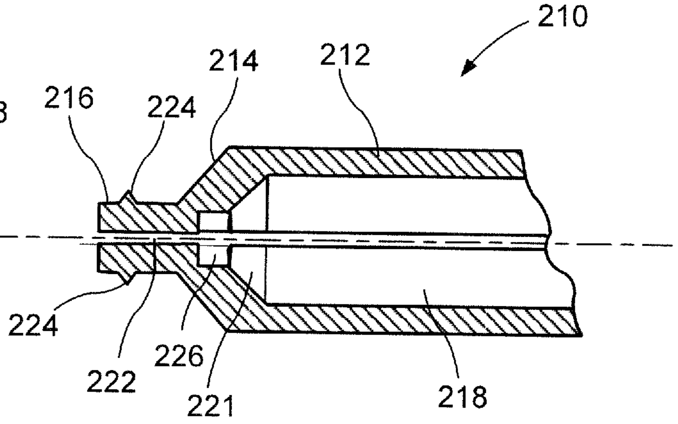
F I G. 3
F I G. 2

SELF-RETAINING SCREWDRIVER WITH SLOTTED TIP

FIELD

The present disclosure relates generally to screwdriver assemblies with slotted and self-retaining tips.

BACKGROUND

A screw may disengage from a screwdriver during the insertion of the screw into a target site. For example, if an intramedullary (IM) nail screw detaches from a self-retaining screwdriver while the physician is guiding the screw into a predrilled hole in a bone, the screw may fall to the floor, get lost in patient soft tissue, or otherwise land outside the sterile field. The problem of retaining the screw on the screwdriver is currently addressed with various hardware including a conical screwdriver tip for gradual interference, a clamp mechanism on the screwdriver to hold a screw in place, a sliding shaft on the screwdriver to force interference, and threaded connections between the screw and the screwdriver. However, existing solutions can add significant cost and complexity to the fixing of a screw to a target anatomy or an implant.

SUMMARY

The present disclosure relates a screwdriver which includes a body extending longitudinally from a proximal end to a distal end. The distal end includes a distal screw engaging tip. The screwdriver also includes a slot extending through a width of the screw engaging tip and extending proximally a distance into the body. The slot permits opposed portions of the screw engaging tip to spread apart from one another into a locking configuration in which the opposed portions apply a radially outward force against an interior surface of a recess in a head of a screw into which the screw engaging tip has been inserted to releasably lock the screw engaging tip within the recess.

In an embodiment, the body includes a lumen extending therethrough to a distal portion adjacent to the screw engaging tip. The screwdriver further includes an insert sized and shaped for insertion into the lumen until a distal end of the insert is received in the distal portion, the distal end of the insert being sized and shaped so that, when received within the distal portion, the distal end of the insert forces the opposed portions of the tip apart to lockingly engage a recess within which the screw engaging tip is received.

In an embodiment, the opposed portions of the screw engaging tip are biased toward a non-engaging configuration in which the opposed portions are drawn together to reduce a profile of the screw engaging tip.

In an embodiment, the lumen includes a tapered section extending between the distal portion and a proximal channel extending to the proximal end of the body.

In an embodiment, the insert includes a tapered section extending between the distal end and a proximal body, a width of the proximal body being greater than that of the distal end.

In an embodiment, a width of a least a portion of the distal end is greater than a width of a corresponding portion of the distal portion to force the opposed portions of the screw engaging tip apart.

In an embodiment, the proximal body further comprises a threading on a proximal portion thereof, the threading corresponding to a complementary threading on an interior of a proximal portion of the proximal channel to facilitate insertion of the distal end into the distal portion.

In an embodiment, a width of a least a portion of the proximal body is greater than a width of a corresponding portion of the proximal channel to force the opposed portions of the screw engaging tip apart.

In an embodiment, the opposed portions of the screw engaging tip are biased toward the locking configuration so that, when forced into a correspondingly sized recess, the bias of the opposed portions forces them radially outward to lockingly engage the recess.

In an embodiment, a distal end of the screw engaging tip includes a chamfer configured to engage an edge of a recess into which the screw engaging tip is to be inserted so that, as a distally directed force is applied to the screwdriver against the edge of the recess, the chamfer forces the opposed portions of the screw engaging tip together so that the tip may be inserted into the recess.

In an embodiment, the slot includes a widened area at a proximal end thereof, a cross-sectional area of the widened being area greater than a cross-sectional area of a distal portion of the slot.

In an embodiment, the screw engaging tip is hexagonal.

In an embodiment, the screw engaging tip has a protrusion extending radially outward therefrom.

In an embodiment, the protrusion forms a ring about a circumference of the screw engaging tip.

In an embodiment, the recess of the screw has an indentation sized and shaped to receive the protrusion therein.

In an embodiment, the screw engaging tip is biased radially outward to a resting state in which a maximum width of at least a portion of the screw engaging tip is greater than a width of a corresponding portion of a recess within which the portion of the screw engaging tip is to be received.

In an embodiment, the screw engaging tip tapers radially outward toward a distal end of the screw engaging tip.

In addition, the present disclosure relates to a screwdriver assembly which includes a screwdriver having a body extending longitudinally from a proximal end to a distal end. The distal end includes a distal screw engaging tip. A slot extends through a width of the screw engaging tip and extending proximally a distance into the body. The slot permits opposed portions of the screw engaging tip to spread apart from one another. The body includes first and second ramped surfaces on opposite sides of the slot. Th screwdriver assembly also includes a sleeve slidably received over the screwdriver body. The sleeve includes a protrusion extending radially inward from an inner surface thereof. The protrusion is sized and shaped so that, as the sleeve is drawn proximally over the body, the protrusion engages the first and second ramped surfaces to force the ramped surfaces apart from one another and widen the slot.

In an embodiment, the slot includes a widened area at a proximal end thereof, a cross-sectional area of the widened being area greater than a cross-sectional area of a distal portion of the slot.

In an embodiment, the screw engaging tip is biased radially outward to a resting state in which a maximum width of at least a portion of the screw engaging tip is greater than a width of a corresponding portion of a recess within which the portion of the screw engaging tip is to be received. Furthermore, the present disclosure relates to a method which includes inserting into a recess in a head of a screw, a distal screw engaging tip at a distal end of a screwdriver in an insertion configuration, the screwdriver having a body extending longitudinally from a proximal end to the screw engaging tip and a slot extending through a width of the screw engaging tip proximally into the body; expanding the width of a distal end of the slot to spread opposed portions of the screw engaging tip apart from one another into a locking configuration to apply a radially outward force against an interior surface of the recess to releasably lock the screw engaging tip within the recess; and returning the slot to the insertion configuration.

In an embodiment, the body includes a lumen extending therethrough to a distal portion adjacent to the screw engaging tip.

In an embodiment, screw engaging tip is expanded to the locking configuration by inserting an insert into the lumen of the body until a distal end of the insert is received in a distal portion of the lumen to force the opposed portions of the screw engaging tip apart.

In an embodiment, the screw engaging tip is expanded to the locking configuration by engaging a threading on an exterior of a proximal portion of the insert with a corresponding threading on an interior of a proximal portion of the lumen and screwing the insert into the lumen.

In an embodiment, the screw engaging tip is returned to the insertion configuration by removing the insert from the lumen and allowing the screw engaging tip to contract under a natural bias.

BRIEF DESCRIPTION

FIG. 1 shows a cross-sectional view of a screwdriver assembly according to a first exemplary embodiment comprising a slotted and cannulated screwdriver.

FIG. 2 shows a cross-sectional view of a screwdriver according to a second exemplary embodiment comprising a protrusion extending radially outward off its distal tip.

FIG. 3 shows a cross-sectional view of a screw according to a second exemplary embodiment for use with the screwdriver of FIG. 2.

DETAILED DESCRIPTION

Figure 4:
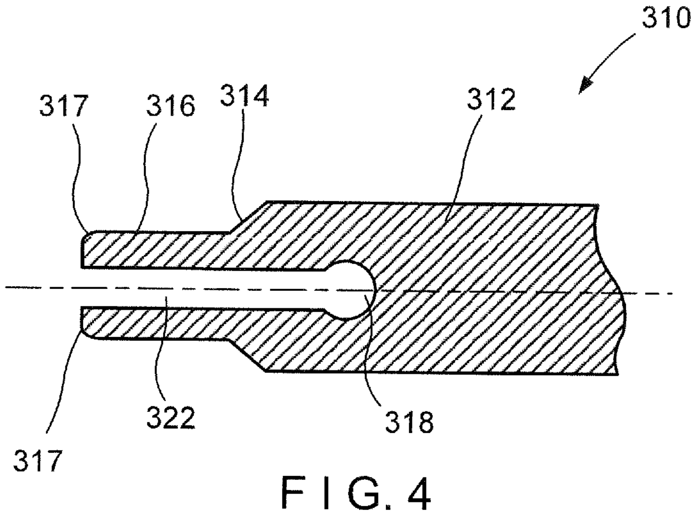
FIG. 4 shows a cross-sectional view of a screwdriver according to a third exemplary embodiment having an oversized distal tip with a slot extending therethrough.

The present disclosure may be further understood with reference to the following description and the appended drawings, wherein like elements are referred to with the same reference numerals. The exemplary embodiments describe self-retaining screwdriver devices and assemblies having slotted screwdriver tips. The devices are configured with a tip that provides a radially outward force, e.g. an expansive force, on the corresponding screw head interior into which the tip has been inserted to retain the screwdriver tip coupled to the screw. The assemblies may also include further features for engaging a screwdriver tip with a screw head and providing a reliable attachment therebetween during the insertion of the screw as well as a simple means for disengagement of the tip from the screw. It should be noted that the terms "proximal" and "distal," as used herein are intended to refer to a direction toward (proximal) and away from (distal) a user of the device.

FIG. 1 shows a screwdriver assembly 100 according to a first exemplary embodiment comprising a slotted and cannulated screwdriver 110. The screwdriver 110 has a cylindrical body 112 with a taper 114 extending to a smaller diameter distal portion (tip) 116 sized and shaped to engage a recess 134 in a head 132 of a screw 130. A slot 122 extends along a centerline of the screwdriver 110 from the distal tip 116 a predetermined distance longitudinally into the body 112, separating the distal tip 116 and a portion of the body 112 into two substantially symmetrical halves.

Those skilled in the art will understand however, that these halves need not be symmetrical and that the slot need not be positioned on or extend along a longitudinal axis of the screwdriver so long as the tip 116 is split into two portions that are separable from one another to spread outward generally transverse to the longitudinal axis of the screwdriver. The two halves of the distal tip 116 are configured to spread away from one another along the slot 122 to press outward against inner surfaces of the recess 134 to firmly engage the distal tip 116 with the screw head 132 after the distal tip 116 has been inserted therein.

The screwdriver 110 is cannulated, having a lumen therein including a large diameter proximal channel 118 extending from a proximal end (not shown) of the screwdriver 110 to open into a distal cavity 120 adjacent to the distal tip 116. The cavity 120 has a diameter smaller than that of the proximal channel 118 and is connected to the proximal channel 118 via a tapered section 121 that gradually widens out from the diameter of the cavity 120 to the diameter of the proximal channel 118. The slot 122 of this embodiment extends through the surface of the screwdriver 110 from an outer surface thereof opening into the hollow interior of the screwdriver 110 proximally from the distal tip 116 along a portion of the length of the screwdriver 110 longitudinally past the distal cavity 120 and the tapered section 121 into the distal portion of the channel 118. A length of the slot 122 is chosen based on considerations including a desired torsional strength of the screwdriver (which may be reduced as the length of the split increases) and a degree of spreading which may also increase as the length of the slot increases. In the exemplary embodiment, the length of the slot 122 may extend up to 100*mm*. Further, the slot 122 may have a widened area (not shown) having a cross-sectional area (an area in a plane perpendicular to a longitudinal axis of the screwdriver 110) greater than that of the slot 122 to facilitate the compression of the halves of the distal tip 116 toward one another.

The channel 118, the tapered section 121 and the distal cavity 120 are sized and shaped to receive an insert 140 therein so that, as the insert 140 is pushed distally into the cavity 120, outer surfaces of the screwdriver on opposite sides of the slot 122 are forced apart as will be described in more detail below. That is, a distal portion of the insert 140 is sized to be slightly larger than a resting shape of the distal cavity 120. Because the outer diameter of the distal portion of the insert 140 is greater than the inner diameter of the cavity 120 as described below, the distal tip 116 of the screw driver will spread apart at the slot 122 so that the halves of the distal tip 116 move radially away from one another as the oversized insert 140 is inserted further distally into the cavity 120.

The insert 140 is shaped similarly to the lumen in the cannulated interior of the screwdriver 110, having a proximal body 142 coupled to a smaller diameter distal end 144 via a tapered section 143. In one embodiment, the distal end 144 of the insert 140 is oversized relative to the cavity 120 in which it fits while the body 142 and the tapered section 143 are sized to fit smoothly into the proximal channel 118 without applying any radially outward force thereto. Those skilled in the art will understand that the distal end 144 may be oversized relative to the distal cavity 120 in any way that results, when the distal end 144 is inserted into the distal cavity 120 in the spreading of the halves of the distal tip 116. For example, if a width of the distal end 144 in one direction (e.g., a direction perpendicular to the longitudinal axis of the screwdriver and to the slot) is greater than a width of the distal cavity 120 in this direction, insertion of the distal end 144 into the distal cavity 120 will spread the halves of the distal tip 120 apart as desired.

Thus, the insert 140 of this embodiment may be inserted with relatively little force through the proximal channel 118 up to the point where the distal end 144 enters the cavity 120, at which time the oversized distal end 144 provides an expansive force against the interior surface of the cavity 120 causing the slot 122 to spread. In another embodiment, a portion of the proximal body 142 of the insert 140 is also oversized so that an expansive force is provided against the interior surface of the proximal channel 118 and the slotted portion of the proximal channel 118 may similarly spread. The degree of expansion of the distal tip 116 resulting from the insertion of the insert 140 may vary based on the relative diameter difference between the insert 140 and the proximal channel 118 and the length of the slot 122.

The insert 140 may be pushed manually into the proximal channel 118, or the insert 140 and proximal channel 118 may be threaded. For example, if only the distal end 144 of the insert 140 is oversized relative to the cavity 120, the body 142 of the insert 140 may be slid into the proximal channel 118 to a given depth until threading at a proximal end of the body 142 engages a corresponding threading on an interior of a proximal portion of the proximal channel 118 to force the oversized distal end 144 into the cavity 120 as the insert 140 is screwed into the proximal channel 118.

The screw 130 for use with the screwdriver 110 of this embodiment may be constructed as is known in the art, e.g. a bone screw having a counter-sinkable head 132 with a recess 134 sized and shaped to receive a complementarily shaped screwdriver tip, i.e. the distal tip 116 of the screwdriver 110 in its unexpanded state, i.e. prior to spreading of the distal tip 116. The recess 134 may be e.g. a hexagonal socket configured to receive a correspondingly sized and shaped hexagonal tip of a screwdriver. The screw 130 has a shaft 136 extending to a distal tip (not shown) insertable into a target hole in e.g. a bone hole and/or implant for securing an IM nail.

To assemble the screw 130 with the screwdriver 110, the distal tip 116 of the screwdriver 110 may be inserted into the recess 134 of the screw head 132 while the screwdriver 110 is in the resting configuration—i.e., while the insert 140 is not inserted into the lumen within the screwdriver 110. The insert 140 is then be inserted through the proximal channel 118 until the distal end 144 of the insert 140 enters the cavity 120 of the proximal channel 118. The expansive force of the oversized insert 140 then spreads the distal tip 116 of the screwdriver 110 along the slot 122, forcing the outer surfaces of the spread tip 116 outward against the inner surfaces of the recess 134 to lock the tip 116 within the recess 134 of the screw head 132. The screw 130 may then be inserted into the target hole to a given depth using the screwdriver 110. After insertion of the screw 130, the insert 140 is removed from the proximal channel 118, releasing the outward force from the distal tip 116 so that the halves of the distal tip 116 spring inward unlocking the distal tip 116 from the recess 134 and allowing the physician to remove the distal tip 116 of the screwdriver from the recess 134.

FIG. 2 shows a screwdriver 210 according to a second exemplary embodiment comprising a protrusion 224 extending radially outward from a distal tip 216 of the screwdriver 210. In all other respects, the screwdriver 210 may be substantially similar to the screwdriver 110 described above with respect to FIG. 1, having a cylindrical body 212 with a taper 214 extending to the distal tip 216. The screwdriver 210 is cannulated with a proximal channel 218 extending from a proximal end (not shown) of the screwdriver 210 to a distal end at which it opens into a distal cavity 220 adjacent to the distal tip 216 via a tapered section 221. Similarly to the distal cavity 120, the distal cavity 220 has a diameter smaller than that of the proximal channel 218 with the tapered section 221 gradually necking down the diameter of the inner surface of the screwdriver 210 from the diameter of the proximal channel 218 to that of the distal cavity 220.

A slot 222 extends through the surface of the screwdriver 210 from an outer surface thereof opening into the hollow interior of the screwdriver 210 and extends from the distal tip 216 along a portion of a length of the screwdriver 210 proximally past the distal cavity 220 and the tapered section 221 into the proximal channel 218 by a predetermined distance. Similar to the slot 122 of the screwdriver 110, the slot 222 may have a widened area (not shown) having a cross-sectional area (an area in a plane perpendicular to a longitudinal axis of the screwdriver 210) greater than that of the slot 222. Those skilled in the art will understand that the protrusion 224 on the distal tip 216 may form a complete ring about a circumference of the distal tip 216 or may be comprised of a series of separate protrusions spaced from one another or in any other desired configuration so long as the geometric arrangement of the protrusion(s) aligns with a geometric arrangement of corresponding recesses formed in the recess of a head of a screw to which the screwdriver 210 is to be coupled.

When the distal tip 216 of the screwdriver 210 is inserted into the recess 134 of the screw head 132 and expanded with the insert 140 in the same manner described above in regard to the screwdriver 110 except that in this case, the protrusion 224 penetrates into the inner surface of the recess 134 by fitting into a preformed indentation within the recess 134 as described below or by forcing itself into the material of the head of the screw 130 to provide further resistance to maintain the coupling between the screwdriver 210 and the screw 130 during a screw insertion procedure.

FIG. 3 shows a screw 230 according to a second exemplary embodiment for use with the screwdriver 210 described above. Similar to the screw 130 described above, the screw 230 comprises a counter-sinkable head 232 with a recess 234 sized and shaped to receive a complementarily shaped screwdriver tip, i.e. the distal tip 216 of the screwdriver 210, and a shaft 236 extending to a distal end (not shown) The head 232 in this embodiment includes an indentation 238 on the inner diameter of the recess 234 having a shape inverse to the protrusion 224 and located at a position complementary to that of the protrusion 224 on the distal tip 216 when the tip 216 is inserted in the recess 234 as desired. When the tip 216 is inserted in the recess 234, the protrusion 224 is received in the indentation 238. When the screwdriver 210 is expanded with the insert 140, as described above, the protrusion 224 is tightly secured in the indentation 238 provide further resistance to retain the screwdriver 210 in the screw 230 during a screw insertion procedure.

FIG. 4 shows a screwdriver 310 according to a third exemplary embodiment having a distal tip 316 with a slot 322 extending therethrough. Similarly to the screwdrivers 110, 210, the screwdriver 310 comprises a body 312 having a first diameter coupled to a distal tip 316 having a diameter smaller than that of the body 312 via a taper 314. However, the screwdriver 310 is slotted only and does not include a cannulation of its proximal end as in the above embodiments. The slot 322 extends proximally through the distal tip 316 a predetermined distance longitudinally into the body 312 to a widened area 318 having a cross-sectional area (an area in a plane perpendicular to a longitudinal axis of the screwdriver 310) greater than that of the slot 322 to facilitate the compression of halves of the distal tip 316 toward one another. Further, the widened area 318 reduces stress at the proximal end of the slot 322.

In this embodiment, the distal tip 316 is biased so that, in a resting state (when not acted on by an outside force) the halves of the distal tip 316 are spread apart from one another so that a distal face of the distal tip 316 is expanded until portions of the distal tip 316 extend radially outward beyond corresponding portions of an opening in the head of a screw into which the distal tip 316 is to be inserted. The outer edges of the perimeter of the distal tip 316 includes a chamfer 317 facilitating the insertion of the distal tip 316 into a recess in the head of a screw that is slightly smaller than the distal tip 316 (in the resting state). That is, as the chamfer 317 engages an outer edge of the recess of a screw, the halves of the distal tip 316 are forced radially inward so that the distal tip 316 enters the recess of the screw with a spring force of the distal tip 316 urging the halves of the distal tip 316 radially outward into engagement with inner surfaces of the recess.

The screwdriver 310 is usable with a screw similar to the screw 130 described above. As described above, the screwdriver 310 has the distal tip 316 which in a resting state is oversized relative to the recess 134 of the screw head 132. In this embodiment, instead of expanding the distal tip via secondary means (i.e. the oversized insert 140 received in the channel 118 of the screwdriver 110), the halves of the distal tip 316 are biased outward to a resting state providing a larger profile than the recess into which it is to be inserted to provide a radially outwardly directed force against the inner walls of the recess 134 when the tip 316 is compressed during insertion into the recess 134. To insert the distal tip 316 in the recess 134, the halves of the distal tip 316 must be compressed due to their oversized shape relative to the recess 134. Thus, the angling of the surfaces of the chamfer 317 with the edges of the recess 134 push the halves radially inward toward one another as slot 322 narrows generating a radially outward spring force in reaction to this compression.

The configuration described above retains the connection between the screw and the screwdriver 310 without requiring any active steps to spread the distal tip 316.

Figure 5:
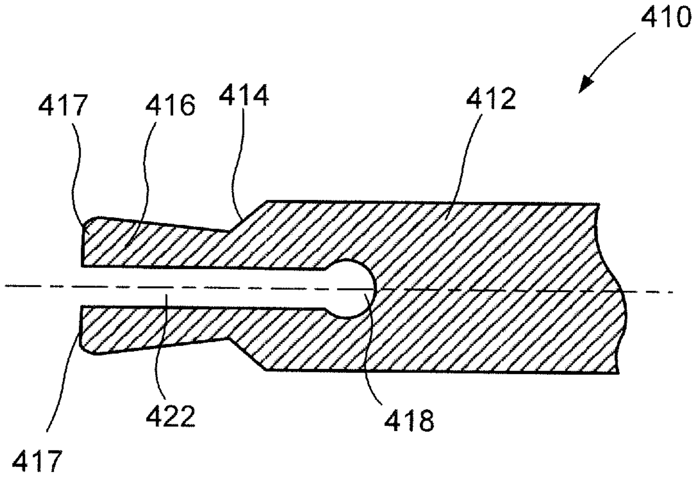
FIG. 5 shows a cross-sectional view of a screwdriver according to a fourth exemplary embodiment having an oversized, tapered distal tip with a slot extending therethrough.

FIG. 5 shows a screwdriver 410 according to a fourth exemplary embodiment having an oversized, tapered distal tip 416 with a slot 422 extending therethrough. The screwdriver 410 is similar to the screwdriver 310 described above, having a cylindrical body 412 with a taper 414 extending to the smaller diameter distal tip 416 with a chamfer 417. The slot 422 extends through the tip 416 a longitudinal distance into the body to an enlarged area 418 having a cross-sectional area greater than that of more distal portions of the slot 422 to facilitate the radially inward compression of the halves of the distal tip 416 in the same manner as described above in regard to the screwdriver 310. However, the distal tip 416 in this embodiment is, in the resting configuration, tapered radially outward (toward a distal end of the distal tip 416) from a proximal end to a distal end, as compared with the distal tip 316 described above with respect to FIG. 4, which, in the resting configuration, is substantially straight. Accordingly, when the halves of the distal tip 416 are compressed radially inward, tapered outer surfaces of the distal tip 416 become parallel to a longitudinal axis of the screwdriver 410.

Similarly to the screwdriver 310 described above, the oversized distal tip 416 is separated into halves by the slot 422 that may be compressed during insertion into the recess of a screw head to provide an outwardly directed force against inner surfaces of the recess of the screwhead as these halves are urged radially outward by a spring force. In this embodiment, the tapered distal tip 416, the when compressed, provides a greater contact area with the inner surface of the recess 134 than a straight tip. Thus, the retention forces between the tip 416 and the recess 134 may be increased.

Figure 7:
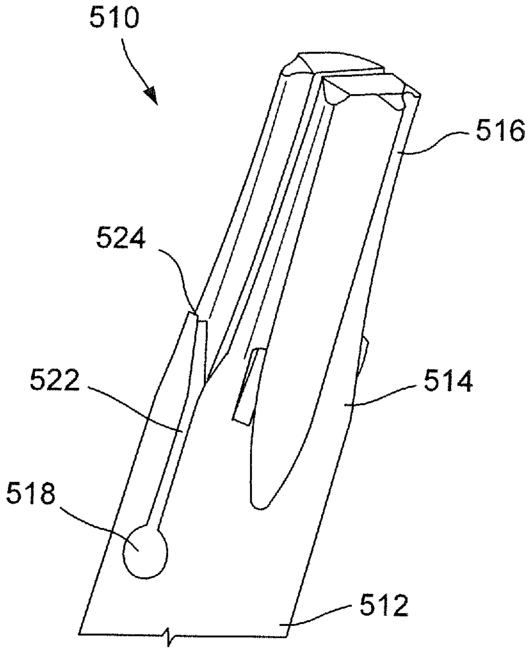
FIG. 7 shows a perspective view of the screwdriver of FIG. 6.
Figure 8:
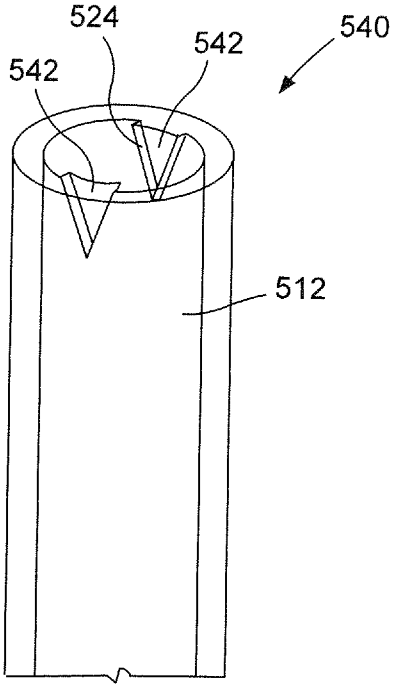
FIG. 8 shows a sleeve configured for use with the screwdriver of FIG. 6.
Figure 6:
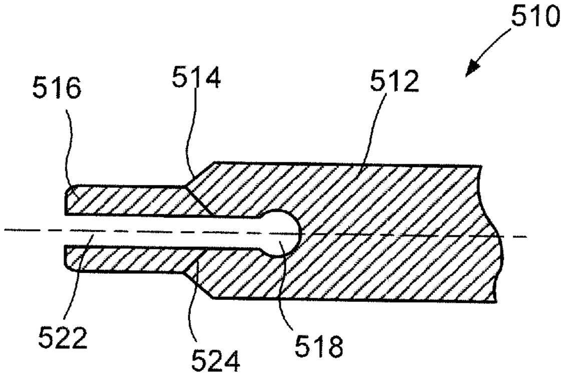
FIG. 6 shows a cross-sectional view of a screwdriver according to a fifth exemplary embodiment having a spreading feature implemented by a sleeve slidable over the distal tip.

FIGS. 6-7 show a screwdriver 510 according to a fifth exemplary embodiment having a spreading feature implemented by a sleeve 540, shown in FIG. 8, slidable over a distal tip 516 of the screwdriver 510. The screwdriver 510 is similar to the screwdriver 310 described above, having a cylindrical body 512 with a taper 514 extending to the smaller diameter distal tip 516. A slot 522 extends proximally through the tip 516 from a distal face of the tip 516 a longitudinal distance into the body 512 to an enlarged area 518. The enlarged area 518 having a cross-sectional area greater than that of the slot 522 to facilitate compression and expansion of the distal tip 516 via halves of the distal tip 516.

The slot 522 in this embodiment passes through a wedge shaped (generally triangular) indent 524 on opposing sides of the outer surface of the body 512. The outer surface of the body 512 has a large open end of the triangular opening indent 524 facing distally so that a correspondingly shaped triangular protrusion 542 extending radially inward from an inner diameter of the sleeve 540 received around the body 512 will enter the large open distal end of the indent 524 as the sleeve 540 is drawn proximally over the body 512. Therefore, as increasingly wide portions of the protrusions 542 enter the indents 524, the halves of the tip 516 are spread apart from one another.

Specifically, FIG. 8 shows the sleeve 540 slidably positioned over the exterior of the screwdriver body 512. In an initial position, the sleeve 540 extends over the body 512 with the protrusions 542 distal of the indents 524. In the exemplary embodiment, an inner surface of the sleeve 540 includes two diametrically opposed two triangular protrusions 542 protruding radially inward from the inner surface of the sleeve 540 toward one another. The interior surface of the sleeve 540 is sized so that it is slidable over and tightly fit to the body 512 of the screwdriver 510. In particular, when the tip 516 of the screwdriver 510 is initially inserted into the recess 134 of the screw 130, the protrusions 542 of the sleeve 540 are distal to the triangular indents 524 of the screwdriver 510 so that the tip 516 is in a resting (non-expanded) state with a proximal portion of the sleeve 540 extending over the screwdriver body 512. As in the earlier embodiments, the tip 516 is configured so that, in the resting state, the tip 516 is sized for easy insertion into the recess 134.

As may be seen more clearly in FIG. 7, the triangular indents 524 of the screwdriver 510 are positioned so that, after the tip 516 has been inserted into the recess 134, and the sleeve 540 is slid proximally relative to the body 512, the triangular protrusions 542 enter the triangular indents 524 and, as the sleeve 540 is drawn further proximally, the protrusions 542 act as wedges forcing the halves of tip 516 to spread apart from one another along the slot 522. Thus, the screwdriver 510 and sleeve 540 may be used to provide a radially expansive force after the screwdriver tip 516 is forced radially outward against the inner surfaces of the recess 134 in the head 132 of a screw 130, to retain a coupling between the screwdriver 510 and the screw 130 as described above in regard to the screwdrivers 110, 210.

As would be understood by those skilled in the art, once the spreading force has been applied, the sleeve 540 may be manually held at its position or may be locked at its engaged position with the screwdriver 510 using any known locking mechanism to maintain the engagement of the screwdriver 510 with the screw 130. Then, the user may disengage the locking of the screwdriver 510 from the screw 130 by releasing the sleeve 540 to move distally allowing the protrusions 542 to move distally out of the indents 524 allowing the tip 516 to spring back to its resting configuration.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiment disclosed, but rather modifications are also covered within the scope of the present invention as defined by the appended claims.

The invention claimed is:

1. A screwdriver, comprising:

a body extending longitudinally from a proximal end to a distal end, the distal end comprising a distal screw engaging tip, the body includes a lumen extending therethrough to a distal chamber proximal of the screw engaging tip, wherein the distal chamber has a distal diameter less than a diameter of a proximal portion of the lumen extending proximally from the distal chamber;

a slot extending proximally through a width of the screw engaging tip from the distal end of the body distally beyond a distal end of the distal chamber, the slot separating opposed portions of the screw engaging tip from one another so that the opposed portions may be spread apart from one another into a locking configuration in which the opposed portions apply a radially outward force against an interior surface of a recess in a head of a screw into which the screw engaging tip has been inserted to releasably lock the screw engaging tip within the recess; and an insert sized and shaped for insertion into the lumen until a distal end of the insert is received in the distal chamber, the distal end of the insert being sized and shaped so that, when received within the distal chamber, the distal end of the insert forces the opposed portions of the screw engaging tip apart to lockingly engage the recess in the head of the screw into which the screw engaging tip has been inserted, wherein the lumen includes a tapered section extending between the distal chamber and a proximal channel extending to the proximal end of the body, wherein the insert includes a tapered section extending between the distal end and a proximal body, a width of the proximal body being greater than that of the distal end, wherein a width of a least a portion of the distal end is greater than a width of a corresponding portion of the distal chamber to force the opposed portions of the screw engaging tip apart, and wherein the proximal body further comprises a threading on a proximal portion thereof, the threading corresponding to a complementary threading on an interior of a proximal portion of the proximal channel to facilitate insertion of the distal end into the distal chamber.

2. The screwdriver of claim 1, wherein the opposed portions of the screw engaging tip are biased toward a non-engaging configuration in which the opposed portions are drawn together to reduce a profile of the screw engaging tip.

3. The screwdriver of claim 1, wherein a width of a least a portion of the proximal body is greater than a width of a corresponding portion of the proximal channel to force the opposed portions of the screw engaging tip apart.

4. The screwdriver of claim 1, wherein the slot includes a widened area at a proximal end thereof, a cross-sectional area of the widened area being greater than a cross-sectional area of a distal portion of the slot.

5. The screwdriver of claim 1, wherein the screw engaging tip is hexagonal.

* * * * *